United States Patent
Pernet et al.

[11] 4,117,014
[45] Sep. 26, 1978

[54] PROSTAGLANDIN DERIVATIVES

[75] Inventors: André G. Pernet, Kirkland, Canada; Hiromasa Nakamoto, Awara; Naoyasu Ishizuka, Ou, both of Japan

[73] Assignee: Abbott Laboratories, North Chicago, Ill.

[21] Appl. No.: 753,115

[22] Filed: Dec. 23, 1976

Related U.S. Application Data

[63] Continuation-in-part of Ser. No. 647,822, Jan. 9, 1976, abandoned.

[51] Int. Cl.$^2$ .................. C07C 49/28; C07C 49/46; C07D 309/06
[52] U.S. Cl. .................. 260/586 R; 260/345.7 P; 260/345.8 P; 260/345.9 P; 260/448.2 B; 260/590 C; 560/9; 560/53; 560/118; 560/121; 562/500; 562/503; 562/463; 542/426; 542/429; C07C/49/82
[58] Field of Search .................. 260/586 R, 448.2 B, 260/345.9, 590 C

[56] References Cited

U.S. PATENT DOCUMENTS

| | | | |
|---|---|---|---|
| 3,873,571 | 3/1975 | Kelly | 260/586 R |
| 3,892,733 | 7/1975 | Brown | 260/586 R |
| 3,923,872 | 12/1975 | Caton | 260/586 R |
| 3,966,792 | 6/1971 | Hayashi et al. | 260/586 R |
| 3,975,442 | 8/1976 | Hajos et al. | 260/586 R |
| 3,981,891 | 9/1976 | Celli | 260/586 R |
| 4,032,576 | 6/1977 | Nelson | 260/586 R |

Primary Examiner—Norman Morgenstern
Attorney, Agent, or Firm—Paul D. Burgauer; Robert L. Niblack

[57] ABSTRACT

Prostaglandin type compounds of the formula

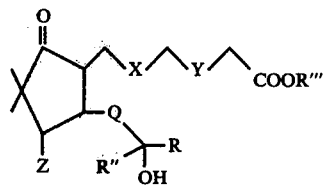

wherein X is —$CH_2$—$CH_2$—, —CH=CH-cis or —C≡C—; Y is $CH_2$ or O; Q is —$CH_2$—$CH_2$—or —CH=CH—; Z is H, OH, $CH_3$ or $CH_2OH$, R is a linear, branched or cyclo alkyl chain of 3 to 7 carbon atoms or certain other moieties, and R" and R"' are H or $CH_3$. These compounds are prepared by essentially a one-step reaction from a new intermediate of the formula

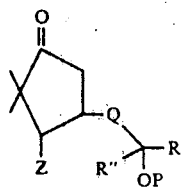

wherein Z, R, R" and Q have the above meaning and P is a removable protective group by condensation with a reactive moiety introducing the entire α-chain (R"'=$CH_3$). If desired, the carbonyl function is subsequently reduced to W= —CH(OH)—. The intermediate is useful in making known and new PGEs useful as antihypertensives, gastric acid secretion inhibitors and smooth muscle stimulants.

16 Claims, No Drawings

PROSTAGLANDIN DERIVATIVES

BACKGROUND OF THE INVENTION

This is a continuation-in-part of our previously filed application Ser. No. 647,822, filed Jan. 9, 1976, now abandoned.

This invention relates to novel prostaglandin derivatives, and more particularly novel prostaglandin E derivatives having useful physiological properties, the method of making these novel derivatives and intermediates useful in making these novel derivatives.

DESCRIPTION OF THE PRIOR ART

The prostaglandins comprise one of the most unique and remarkable groups of chemical compounds to emerge in recent years. Extensive research with these agents, conducted largely during the last decade, has provided new insights in the fundamental biological processes and has offered a promise of new potent therapeutic agents.

Chemically, the prostaglandins are fatty acids of up to 20 carbon atoms with contain a 5-membered ring, having 2 attached aliphatic side chains, one carrying a carboxylic acid group at the terminus. The basic structure, prostanoic acid, is shown as I.

I

Chemical variations, involving hydroxyl, carbonyl, and structural variances such as unsaturated groups from the various prostaglandins. An abbreviation system for naming these agents is widely used. Following the letters of PG (prostaglandin), the designation of A, B, E, and F is used to denote the specific ring structure. For example, prostaglandin $E_1$ ($PGE_1$) has the following structure:

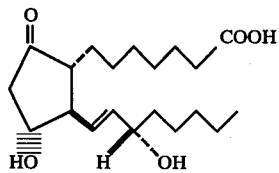
II

Prostaglandin $E_2$ ($PGE_2$) has the following structure:

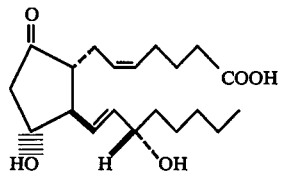
III

In structures II and III, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring. See *Nature*, 212, 38 (1966) for discussion of the stereochemistry of the prostaglandins.

The prostaglandins are synthesized in the body from poly-unsaturated fatty acids by the formation of a five-membered ring (cyclopentane ring) and incorporation of three oxygen atoms at certain positions. One of the common fatty acid precursors who are natural prostaglandins is arachidonic acid, the precursor of prostaglandin E2.

The main source of arachidonic acid is the phospholipids, which are found in the cell membrane.

The $PGE_2$ compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. $PGE_2$ is also useful as an hypotensive agent to reduce blood pressure in mammals, including man. $PGE_2$ also increases the flow of blood in the mammalian kidney, thereby increasing volume and electrolyte content of the urine. Therefore, the compound is useful in managing cases of renal disfunction, especially those involving blockage of the renal vascular bed.

DETAILS OF THE INVENTION

The new derivatives of this invention are related to prostaglandin E's, which, as previously indicated, are potent naturally occurring vasodilators, gastric secretion inhibitors and smooth muscle stimulants. However, prostaglandin E's are subject to rapid metabolic change and therefore have a very short half-life in the body. The novel derivatives described herein have useful pharmacological properties similar to PGEs, but have a much longer half-life in the body because of their increased resistance to metabolic change. The metabolizing enzymes which convert PGEs to partially or totally inactivated products include:

(a) PGE dehydration occurring mainly in the blood plasma, which converts PGEs to PGAs and ultimately to PGBs;

(b) 15-hydroxydehydrogenase, present in the lung and the renal cortex, which oxidizes the 15-hydroxyl to the 15-oxo derivative; and (c) oxidizing enzymes which cause oxidation in the α-chain and ω and ω-1 oxidation in the ω-chain.

The compounds of the present invention have the formula

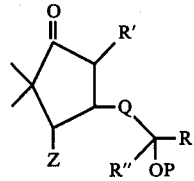
IV wherein R' is H or $CH_{2-X-CH2}$—Y—$CH_2$—COOR"; X is $CH_2$—$CH_2$, or —CH=CH—; Y is $CH_2$ or O; Z is H, OH, $CH_3$, $CH_2OH$, R is a linear, branched or cyclo alkyl chain of 3 to 7 carbons, trifluoromethylbutyl, hydroxyalkyl, or —$CH_2$—R''' wherein R''' is phenyl, cyclopentyl, phenoxy, chlorophenoxy, propoxy or —$CH_2SCH_2CH_3$, R" is H or methyl, Q is —$CH_2$—$CH_2$— or —CH=CH—, and P is hydrogen or a protective group that can be removed without affecting the rest of the molecule. The compound wherein R' is hydrogen can be converted into the compounds of R"≠H, where P≠H and R' ≠ H, the compounds can be modified so as to resist isomerization, dehydrogenation and oxidation, but retain the pharmacological properties characteristics of the PGEs.

It has been found that PGs of various α-chains can be made through a new synthetic route (FIG. 1) involving, as a new intermediate, the above 5-unsubstituted, 5-membered ring (R'=H). This intermediate can then be treated, in known fashion, to prepare the PGs with known α-chains. The compounds are prepared by essentially a one-step reaction with a novel intermediate of formula IV where R'=H, Q, R, R" and P have the above meaning, and Z is H, OP, $CH_3$ or $CH_2OP$.

The novel preparation of the modified PGs involves the 1,4-addition of a cuprate reagent (containing the entire ω-chain) to the compound of formula V.

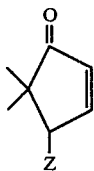
V

This step is followed by a second alkylation, α to the carbonyl, in which the entire α-chain is added (FIG. 1).

sive secretion of gastric acid such as, for example, peptic ulcer.

When the compounds of this invention are employed as hypotensive or anti-hypertensive agents, or agents inhibiting gastric acid secretion in warm-blooded animals, for example, in cats or rats, as agents for the prevention or treatment of thrombosis, or as bronchospasmolytic agents, alone or in combination with pharmaceutically acceptable carriers, their proportions are determined by their solubilities, by the chosen route of administration, and by standard medicinal practice. The compounds of this invention may be administered orally in solid form containing such excipients as starch, lactose, sucrose, certain types of clay, and flavoring and coating agents. However, they are preferably administered parenterally in the form of sterile solutions thereof which may also contain other solutes, for example, sufficient sodium chloride or glucose to make the solution isotonic. For use as broncho-spasmolytic agents, the compounds of this invention are preferably administered as aerosols.

The dosages of the present hypotensive, antihypertensive, gastric acid secretion inhibiting, or bronchospasmolytic agents, or agents for the prevention and treatment of thrombosis will vary with the forms of administration and the particular hosts under treatment.

FIG. 1

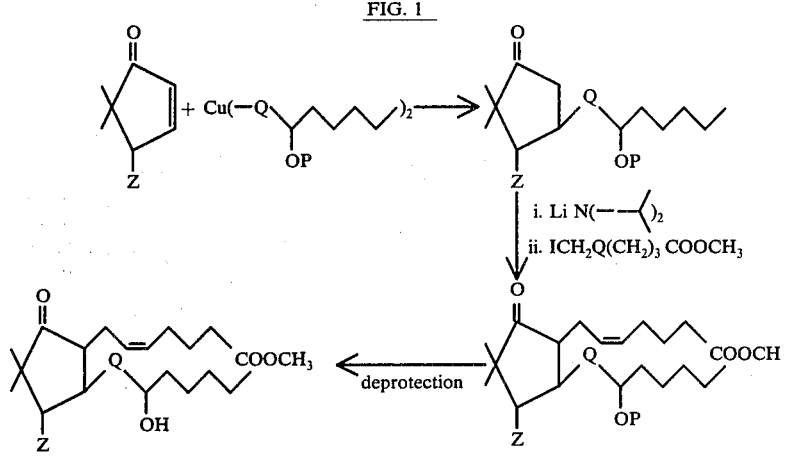

where P is a protective group such as t-butyldimethylsilyl or tetrahydropyranyl.

The term "protective group" as used herein refers to a group such as t-butyl-dimethylsilyl or tetrahydropyranyl which can be removed without affecting the rest of the molecule. Other examples of such protective groups are well known to those familiar with the art.

The compounds of the formula

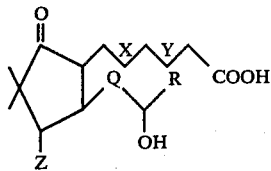

possess interesting pharmacological properties when tested in standard pharmacological tests. In particular, they have been found to possess hypotensive, antihypertensive and gastric acid secretion inhibiting properties which make them useful in the treatment of conditions associated with high blood pressure and in the treatment of pathological conditions associated with exces- Generally, treatments are initiated with small dosages substantially less than the optimum doses of the compounds. Thereafter, the dosages are increased by small increments until the optimum effects under the circumstances are reached. In general, the compounds of this invention are most desirably administered at a concentration level that will generally afford effective results without causing any harmful or deleterious side effects and preferably at a level that is in a range of from about 0.1 μg to about 10.0 μg per kilo, although as aforementioned variations will occur. However, a dosage level that is in range of from about 0.5 mg to about 5 mg per kilo is most desirably employed in order to achieve effective results. When administering the compounds of this invention as aerosols, the liquid to be nebulized, for example, water, ethyl alcohol, dichlorotetrafluoroethane and dichlorodifluoromethane, contains preferably from 0.005–0.05 percent of the acid, or a non-toxic alkali metal, ammonium or amine salts thereof, or ester of Formula IV.

In order to illustrate the procedures for making the compounds of the present invention, reference is made to the following examples which, however, are not meant to limit the invention in any respect. In all instances, the structures of the compounds prepared were confirmed by microanalysis, IR- or nmr spectra and/or other methods ordinarily used for such purpose.

EXAMPLE 1

2,2-Dimethyl-4-(3'-t-butyldimethylsilyloxy-1'-octenyl)-cyclopentan-1-one (a) A solution of 8 g of t-BuLi in 100 ml pentane was added to 20.28 g of 1-iodo-3-t-butyldimethyl-silyloxy-trans-1-octene (obtained as described by Corey JACS 94, 7210 of 1972) in 240 ml ether over a period of 40 min. at −70° to −72° C. under nitrogen. The mixture was stirred at that temperature for two hours. Independently, 7.98 ml $nBu_3P$ was added to a suspension of 5.712 g of CuI in 156 ml of ether. After 30 minutes, this clear solution was added over a period of 30 min. to the above solution of the vinyl lithium compound at −70° to −72° C. The resulting mixture was stirred for 1 hour. At that point the solution was a faintly yellow suspension.

(b) A solution of 3.3 g of 2,2-dimethylcyclopent-4-en-1-one, (described by T. Matsumoto in Bull.Chem.Soc. Japan, 45, 1140 of 1972) in 180 ml ether was added to the above yellowish suspension at −70° to −67° C. and stirred for 15 min. The solution turned slightly yellowish orange. Stirring was prolonged at −71° to −67° C. for 30 min. more, then the temperature was raised to −15° C. in the following 9 min. and the mixture was stirred another 30 min. at which time 1N HCl was added. After 3 min. the temperature rose to 12° C. and the solution turned black. The solution was stirred at 12° to 19° C. for 22 min. After adding 240 ml of a 20% aqueous ammonium sulfate solution, the mixture was stirred at 21° to 22° C. for 30 min. The ethereal layer was separated, washed with 240 ml saturated NaCl aqueous solution, dried over $MgSO_4$ and concentrated to give 27.302 g of a slightly yellow oil. The product was chromatographed over a silica gel column to remove the less polar impurities, such as $(n-Bu)_3P$, vinyl by-product, etc. using ethyl acetate-n-hexane 1:7 as the eluant. After elution with 1490 ml of this solvent, the following fraction (900 ml) containing the desired compound was concentrated to give 6.731 g of colorless oil of the title compound. Yield: 69.8%.

EXAMPLE 2

Preparation of methyl 7-iodo-cis-5-heptenoate

Methyl 7-hydroxy-5-heptynoate (3.9 g) was hydrogenated in the presence of 400 mg of 5% palladium-on-carbon and 1 g of quinoline in 50 ml methanol. The mixture was filtered and the methanol concentrated. The residue was dissolved in dichloromethane and washed twice with water, dried and concentrated to give 3.8 g of 7-hydroxy-5-heptenoate.

The product (3.8 g) was stirred at room temperature for six hours with 12.4 g of $(PhO)_3PCH_3I$ in 25 ml of $CH_2Cl_2$/DMF (4:1). After the organic phase was washed with water, dried and concentrated, the residue was purified by column chromatography and eluted with petroleum ether (30–60°) to yield the desired 7-iodo-cis-5-heptenoate.

EXAMPLE 3

11-Deoxy-10,10-dimethyl-$PGE_2$ and methyl ester (a) A solution (8.3 ml) of 382 mg methyllithium in $Et_2O$ was added to 35 ml dimethoxyethane at −50° C. A solution of 2.43 ml diisopropylamine in 5 ml DME was dropwise added to the ethereal solution of methyllithium at −40° to −35° C for 2 min. and stirred to make diisopropyl lithium amide at −30° to −20° C for 15 min. A solution of 2.786 g of the compound in 12 ml DME was dropwise added to the solution of diisopropyl lithium amide at −25° to −20° C for 10 min. and stirred at −20° to 0° C for 1 hr. The solution turned reddish brown. The above solution was rapidly warmed to 25° C. with stirring, and then 4.636 g of the iodide of Example 2 in 5 ml DME was added to the solution at 25° to 32° C. in 2 min. and stirred at 30° to 33° C. for 1 hr. The resulting solution was cooled to −15° C. and acidified with 17.5 ml 1 N HCl at −17° to −14° C., followed by the addition of 40 ml of a 20% aqueous solution of $(NH_4)_2SO_4$ for the salting out. The liquid was extracted with two 50 ml portions of $CH_2Cl_2$. The combined $CH_2Cl_2$ extract was washed with 100 ml saturated NaCl aqueous solution, dried with $MgSO_4$ and concentrated to give 6.753 g of reddish brown oil. This product was purified by column chromatography, first on silica gel, using EtOAc—$CH_2Cl_2$ as the eluant, and then on silica gel with EtOAc-n-hexane as the eluant. The fraction containing the desired compound was concentrated to give 790 mg of colorless oil which showed one major spot on TLC ($R_f$ 0.67, EtOAc—$CH_2Cl_2$;1:15).

(b) The mixture of 790 mg of the above compound and 162 mg of p-toluene sulfonic acid, monohydrate in 8.6 ml methanol was stirred at 0° to 3° C. for 6 hrs. The reaction mixture was poured into 20 ml saturated aqueous $NaHCO_3$ solution, then extracted with $CH_2Cl_2$ (10 ml × 3). The combined $CH_2Cl_2$ layer was washed with 10 ml water, dried with $MgSO_4$ and concentrated to give 615 mg of a yellow oil. This product was purified by placing it on a silica gel column which was eluted with acetone-$CHCl_3$ 1:20. Discarding the first 90 ml of this eluate, the following 400 ml fraction containing the desired compound was concentrated to give 525 mg of colorless oil which showed one major spot on TLC ($R_f$ 0.54, acetone-$CHCL_3$;1:10). Title compound R'''=Me.

(c) A suspension of 462 mg of the above compound in 19.5 ml of McIlvaine-buffer solution (pH 7.0) and 29.3 ml lipase solution (56745 unit) were stirred under nitrogen atmosphere at 30° to 33° C. for 16 hrs. Cold acetone (49 ml) and 2.5 g of hyflo super-cel were added to the mixture in order to precipitate the proteins. The mixture was filtered and the residue was washed with cold acetone (49 ml). The combined filtrate was concentrated to about 40 ml, extracted with 3 portions of 49 ml each of EtOAC, dried with $MgSO_4$ and evaporated in vacuo to give 346 mg of slightly yellow syrup. The crude syrup was purified by column chromatography on silica gel, eluted with $CHCl_3$-acetone 3:1. The first 93 ml of the solvent extracted 100 mg of colorless syrup representing the starting material for this step. The next 80 ml fraction contained the desired compound; it was evaporated to afford 238 mg of colorless syrup. The crude syrup was repurified by column chromatography on silica gel, eluted with $CHCl_3$-acetone 5:1. After elution with 120 ml of the solvent, the following 120 ml fraction was concentrated to give 205 mg of slightly yellow viscous syrup which showed one major spot on TLC ($R_f$ 0.34, CHCl$_3$-acetone 3:1). Yield 46.2% of 10,10-dimethyl-11-deoxy-PGE$_2$ = Compound IV: P,R",Z=H; Q = —CH=CH—; R' = —CH$_2$–$_{CH=}$ $_{CH-(CH_2)_3}$COOH.

EXAMPLE 4

10,10-Dimethyl-PGE$_2$

By replacing the starting material for the process in Example 1 (b) with 2,2-dimethyl-3-acetoxycyclopent-4-en-1-one (same reference) and using 1-iodo-3-tetrahydropyranyloxy-trans-1-octene for the ω-chain, the procedure of Example 3 produces the compound of structure IV wherein Q = —CH=CH—; R = nC$_5$H$_{11}$; Z = OH; P,R", R''' = H; by way of the corresponding methyl ester (R''' = Me), with R' being CH$_2$CH=CH(CH$_2$)$_3$COOH. ($R_f$ 0.38, CHCl$_3$-MeOH 8:1).

EXAMPLE 5

11-Deoxy-10,10-dimethyl-13,14-dihydro-PGE$_1$

A solution of 1.637 g of the compound of Example 3 (c) in 16 ml EtOAc was hydrogenated at 1° C. for 86 min. in the presence of 327 mg of 5% Pd/C. The catalyst was filtered off and the product isolated as a colorless syrup after evaporation of the solvent under reduced pressure ($R_f$ 0.29, CHCl$_3$-acetone 3:1).

EXAMPLE 6

11-Deoxy-13,14-dihydro-10,10,15-trimethyl PGE$_1$

Jones reagent (0.77 ml) was added rapidly to the solution of 850 mg of the compound of Example 5 in 17 ml acetone at −45° C, and stirred at −31° to −9° for 30 min. After adding 69 ml water to the reaction mixture, it was extracted with EtOAc (23 ml × 3). The combined extracts were washed with water, dried over anhydrous MgSO$_4$, and evaporated in vacuo to give 803 mg of a colorless syrup in a yield of 95.0%, which showed one spot on TLC (Rf 0.62, CHCl$_3$-acetone 3:1). The solution of 130 mg CH$_3$Li in 2.8 ml Et$_2$O was added dropwise to the solution of the 721 mg of the above compound in 14 ml THF (14 ml) at −68° to −55° C. in 3 min. and stirred at −60° to 55° C. for 30 min. under an N$_2$ atmosphere. 1N-HCl (10 ml) was added to the reaction mixture at −60° to −18° followed by 28 ml of water. The mixture was extracted with EtOAc (14 ml × 3) and the combined extracts were washed with water and dried over anhydrous MgSO$_4$. The solution was evaporated in vacuo to leave 783 mg colorless syrup, which was chromatographed on silica gel M, eluting the product with CHCl$_3$-acetone 5:1. This eluate was rechromatographed in the same fashion, discarding the first 70 ml of the solvent. The following 120 ml eluate contained the desired compound which was isolated by evaporating the solution in vacuo to yield 305 mg of a colorless syrup. R'=—(CH$_2$)$_6$COOH; Z=P=H; R=nC$_5$H$_{11}$; Q=CH$_2$CH$_2$ and R"=CH$_3$.

EXAMPLE 7

11-Deoxy-13,14-dihydro-10,10,15-trimethyl-PGE$_2$

By using the procedure of Example 6 with the compound of Example 1 (b) and proceeding subsequently as in Example 3 (a,b,c), the PGE$_2$ analog of Example 6 was obtained.

EXAMPLE 8

11-Deoxy-13,14-dihydro-10,10-dimethyl-PGE$_2$

By using the procedure of Example 5 on the compound of Example 1 (b) followed by the process shown in Example 3 (a,b,c), the PGE$_2$ analog of the compound of Example 5 was obtained. This compound has similar but higher physiological activity than PGE$_2$ with reduced side effects.

EXAMPLE 9

11-Deoxy-10,10,15-trimethyl-PGE$_2$

By using the procedure of Example 6 with the compound of Example 3 (c), the double bonds in both sidechains were retained while introducing an additional methyl group in the ω-chain.

EXAMPLES 10–13

Other 11-deoxy-10,10-dimethyl-PGE$_2$ Derivatives

By proceeding according to the entire sequence of Examples 1–3 but starting with 1-iodo-3-tetrahydropyranyloxytrans-1-decene, the homolog to the compound of Example 3 was made.

In the same fashion, but starting with 1-iodo-3-t-butyldimethylsilyloxy-7,7-dimethyl-trans-1-octene, the corresponding PGE$_2$ derivative with a tertiary terminal in the ω-chain was obtained ($R_f$ 0.34, CHCl$_3$-acetone 3:1).

Using the same sequence with 1-iodo-3-tetrahydropyranyloxy-4,4-dimethyl-trans-1-decene or 1-iodo-3-t-butyldimethylsilyloxy-8,8,8-trifluoro-trans-1-octene, the 11-deoxy-10,10-dimethyl PGE$_2$ analogs were obtained carrying a 16,16-dimethyl or a 20,20,20-trifluoro modification, respectively ($R_f$ 0.39, CHCl$_3$-acetone 3:1 for the latter).

EXAMPLE 14

Using the sequence of Examples 1–3 but starting with 3-acetoxymethyl-2,2-dimethylpent-4-en-1-one, the procedure of 1(b) produced the 3-acetoxymethyl derivative of Example 1 (b) in a yield of 83.7%. The acetyl group was removed and the hydroxy group protected with the same protective group as in the 3'-position (yield for both steps: 78.5%). The α-chain of Example 2 was introduced in a yield of 44%. Removal of the protective groups and the methyl ester group was done in a substantially quantitative yield.[α]$_D^{20}$ 46.7°.

EXAMPLE 15

Compound IV: Q= —CH=CH—; R=benzyl; P,Z,R"=H; R' = —CH$_2$CH=CH(CH$_7$)$_3$COOR'''

(a) 4,4-Dimethyl-3-oxocyclopentylcarboxylic acid was esterified to the corresponding ethyl ester (90.4% yield) followed by the conversion of the oxo group to the ethylene glycol ketal (76%), following well-known reaction techniques. This compound was reduced with sodium-bis(2-methoxyethoxy) aluminum hydride in benzene under N$_2$ to produce the ketal of the corresponding cyclopentylmethanol (99.9%) which was converted to the corresponding aldehyde, using C$_r$O$_3$ in methylenechloride and pyridine (67.2%).

(b) Trimethylphosphite (124.1 g) was dropwise added to 7.1 g methyliodide at 95°–98° over 15 min. and the mixture was stirred 1 hr. at 98°. Distillation under reduced pressure produced 99% yield of dimethyl methane phosphate. A solution of 22.4 g of this compound in 15 ml THF was dropwise added to a stirred solution of 122 ml of a 10% n-BuLi/hexane in 75 ml. THF at −68° to −60° for 40 min. After stirring this mixture under $N_2$ for ½ hr. at this temperature, 16.4 g of ethyl phenylacetate in 10 ml THF was added; stirring was continued for 3 hrs. at −68°. By adding water and 6N HCl, the phases separated. The aqueous phase was extracted with $CH_2Cl_2$ which solution was worked up in the usual fashion to produce dimethyl phenylacetylmethane phosphonate (35% yield).

(c) A $CH_2Cl_2$ solution of 6.43 g of this compound was dropwise added to 1.81 g of $C_2H_5ONa$ in $CH_2Cl_2$ and after stirring for 1 hr. at room temperature, 3.26 g of the above aldehyde in $CH_2Cl_2$ was added. Under standard work-up procedures, the desired 4,4-dimethyl-3-(ethylene glycol ketal)-1-(4-phenyl-3-oxo-1-butenyl)cyclopentane was obtained in a yield of 66.6%. The oxo-group was reduced to the hydroxy group with $LiAlH_4$ (97.6%); the ketal was removed by heating the compound in 1N HCl (99.5%) and the free hydroxy group was again protected, using tetrahydro pyranyl as the protecting group (68%).

(d) Following the procedure of Example 3 (a,b,c) with this compound as the starting material yields the title compound. Yield over the three steps was 20.5%.

EXAMPLES 16–18

Compound IV; Q= —CH=CH—; R=(chloro)benzyl; P,Z,R"=H; R'=CH$_2$CH=CH(CH$_2$)$_3$COOR'"

Following Example 15 but using ethyl 3-chlorophenoxyacetate, ethyl 2-chlorophenoxyacetate or ethyl phenoxyacetate, respectively, in place of ethyl phenylacetate, the final compounds obtained were the PGE$_2$ analogs of Example 15 wherein R (of structure IV) is 3-chlorophenoxymethyl, 2-chlorophenoxymethyl or phenoxymethyl.

EXAMPLES 19–22

Other analogs of Example 15: R=hydroxyalkyl, cycloalkylalkyl, alkylthiaalkyl or alkoxyalkyl In the same fashion as shown in Example 15, but replacing the ethyl phenylacetate with ethyl 4-hydroxypentanoate, ethyl cyclopentylacetate, ethyl ethylthiapropionate or ethyl propoxyacetate produced the corresponding PGE$_2$ derivatives carrying in the R-position of formula IV (Q=CH=CH, P,Z,R"=H, R'=CH$_2$CH=CH(CH$_2$)$_3$COOH) the radicals —(CH$_2$)$_3$—CHOHCH$_3$,

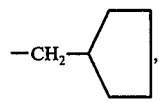,

—(CH$_2$)$_2$SC$_2$H$_5$, or —CH$_2$O(CH$_2$)$_3$H, respectively. The first of these derivatives is the 19-hydroxy analog of the compound of Example 3 (c); the last two are the 18-thia- and the 17-oxa-analogs of 11-deoxy-10,10-dimethyl-PGE$_2$.

It will be obvious to those skilled in the art that the basic procedures detailed in the examples can be carried out with almost any of the possible starting materials involved here. Thus, the methods shown in Examples 1,3 and 5–22 can be carried out with 2,2,3-trimethoxycyclopentenone as easy as with the 2,2-dimethyl compound used above. Similarly, the procedure of Example 4 can be carried out with the starting material that carries a 3-acetoxymethyl group. Also, the methods shown in Examples 5–12 can be used to modify any and all of the compounds shown in Examples 13–22, thus producing both, the PGE$_1$ and PGE$_2$ analogs of the compounds specifically illustrated. Similarly, the compounds wherein the α-chain contains Y=O are made as shown above, using known techniques of the prostaglandin art.

While the above examples show the introduction of the α-chain into the molecule by means of a methyl ester, it will be obvious to those skilled in the art that other esters can be used in the same fashion, primarily loweralkyl esters.

We claim:
1. A compound of the formula

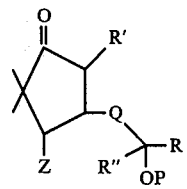

wherein Z is H or CH$_3$, OP or CH$_2$OP; P is H or a protective group that can easily be removed without affecting the rest of the molecule; R' is H; Q is —CH$_2$—CH$_2$— or —CH=CH—;; R is a linear, branched or cyclic alkyl of 3 to 7 carbons, trifluoromethylbutyl, hydroxyalkyl or —CH$_2$R'" where R'" is phenyl, cyclopentyl, phenoxy, chlorophenoxy, propoxy or —CH$_2$SCH$_2$CH$_3$; and R" is H or CH$_3$.

2. A compound according to claim 1 wherein R' is H, Z is H, OP, CH$_2$OP or CH$_3$ and R" is H or CH$_3$.

3. The compound of claim 2 wherein P is t-butyldimethylsilyloxy.

4. The compound of claim 2 wherein P is tetrahydropyranyl.

5. A compound according to claim 1 wherein R' is H and Z is H.

6. A compound according to claim 5 wherein Q is CH=CH.

7. A compound according to claim 6 wherein R"=P=H.

8. A compound according to claim 6 wherein R" is CH$_3$.

9. The compound of claim 7 wherein R is trifluoromethyl-n-butyl.

10. The compound of claim 7 wherein R is 3-chlorophenoxymethyl.

11. The compound of claim 7 wherein R is 2-chlorophenoxymethyl.

12. The compound of claim 7 wherein R is phenoxymethyl.

13. The compound of claim 7 wherein R is ethylthiaethyl.

14. The compound of claim 7 wherein R is propoxymethyl.

15. A compound according to claim 5 wherein Q is —CH$_2$—CH$_2$—.

16. The compound of claim 15 wherein R is 2-hexyl and P and R" are H.

* * * * *